(12) United States Patent
Song et al.

(10) Patent No.: US 9,691,168 B2
(45) Date of Patent: Jun. 27, 2017

(54) IMAGE RECONSTRUCTION USING GRADIENT PROJECTION FOR MEDICAL IMAGING APPLICATIONS

(75) Inventors: William Youngjae Song, San Diego, CA (US); Chunjoo Park, San Diego, CA (US); Bongyong Song, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 44 days.

(21) Appl. No.: 14/006,088

(22) PCT Filed: Mar. 18, 2012

(86) PCT No.: PCT/US2012/029591
§ 371 (c)(1),
(2), (4) Date: Nov. 27, 2013

(87) PCT Pub. No.: WO2012/129140
PCT Pub. Date: Sep. 27, 2012

(65) Prior Publication Data
US 2014/0086467 A1 Mar. 27, 2014

Related U.S. Application Data

(60) Provisional application No. 61/454,387, filed on Mar. 18, 2011.

(51) Int. Cl.
*G06K 9/00* (2006.01)
*G06T 11/00* (2006.01)
*A61B 6/00* (2006.01)

(52) U.S. Cl.
CPC .......... *G06T 11/006* (2013.01); *A61B 6/5205* (2013.01); *G06T 2211/424* (2013.01)

(58) Field of Classification Search
None
See application file for complete search history.

(56) References Cited

U.S. PATENT DOCUMENTS

2003/0156684 A1 8/2003 Fessler
2006/0285606 A1 12/2006 Khojastepour et al.
(Continued)

OTHER PUBLICATIONS

Figueiredo et al., "Gradient projection for sparse reconstruction: application to compressed sensing and other inverse problems", IEEE Journal of Selected Topics in Signal Processing, vol. 1, No. 4, Dec. 2007.*

(Continued)

*Primary Examiner* — Soo Jin Park
(74) *Attorney, Agent, or Firm* — Perkins Coie LLP

(57) ABSTRACT

Techniques and systems are disclosed for estimating an unknown image from a plurality of cone-beam computed tomography (CBCT) image projections. The unknown image is estimated by solving for minima of an expression comprising a fidelity term that is a function of the plurality of image projections and a regularization term that is responsive to a sparsity of the CBCT image projections. The minima of the expression is iteratively estimated by calculating an image gradient of the function, determining a step size based on a based on a Barzilai-Borwein (BB) formulation and adjusting the minima estimate using the projected image gradient and a step size.

22 Claims, 5 Drawing Sheets

(56) References Cited

U.S. PATENT DOCUMENTS

2007/0217566 A1   9/2007   Chen et al.
2013/0002659 A1*  1/2013   Jiang et al. .................. 345/419

OTHER PUBLICATIONS

Choi et al., "Compressed sensing based cone-beam computed toography reconsturction with a first-order method", Medical Physics 37 (9), Sep. 2010.*

Shi et al., "Step-size estimation for unconstrained optimization methods", Computational & Applied Mathematics, vol. 24, No. 3, pp. 399-416, 2005.*

Yuan et al., "Step-sizes for the gradient method", AMS/IP Studies in Advanced Mathematics, 2008.*

Raydan et al., "Relaxed steepest descent and Cauchy-Barzilai-Borwein method", Computational Optimization and Applications, 21, 155-167, 2002.*

Barzilai, J. et al., "2-point step size gradient methods," Ima, J. Numer. Anal. 8(1), 141-148 (1988).

Bian, J. et al., "Evaluation of sparse-view reconstruction from flat-panel-detector cone-beam CT," Phys. Med. Bio.I 55 (22), 6575-6599 (2010).

Candes, E. J. et al., "Robust uncertainty principles: Exact signal reconstruction from highly incomplete frequency information," IEEE. Trans. Inform. Theory. 52(2), 489-509 (2006).

Chen, G. H. et al., "Prior image constrained compressed sensing (PICCS): a method to accurately reconstruct dynamic CT images from highly undersampled projection data sets," Med. Phys. 35(2), 660-663 (2008).

Yoo, S. et al., "Dosimetric feasibiiity of cone-beam CT-based treatment planning compared to CT-based treatment planning," Int. J. Radiat. Oncol. Biol. Phys. 66(5), 1553-1561 (2006).

Donoho, D. L. et al., "Stable recovery of sparse overcomplete representations in the presence of noise," IEEE. Trans. Inform. Theory. 52(1), 6-18 (2006).

Donoho, D. L., "Compressed sensing," IEEE. Trans. Inform. Theory. 52(4), 1289-1306 (2006).

Feldkamp, L. A. et al., "Practical cone-beam algorithm," J. Opt. Soc. Am. A. 1(6), 612-619 (1984).

Xu, F. et al., "Real-time 3D computed tomographic reconstruction using commodity graphics hardware," Phys. Med. Biol. 52(12), 3405-3419 (2007).

Hatton, J. et al., "Cone beam computed tomography: The effect of calibration of the Hounsfield unit number to electron density on dose calculation accuracy for adaptive radiation therapy," Phys. Med. Biol. 54(15), N329-346.

Hoon, K. T., Authorized Officer, Korean Intellectual Property Office, International Search Report, International Application No. PCT/US2012/029591, Sep. 27, 2012, 8 pages.

Jaffray, D. A. et al., "Flat-panel cone-beam computed tomography for image-guided radiation therapy," Int. J. Radiat. col. Biol. Phys. 53(5), 1337-1349 (2002).

Jaffray, D. A., "Emergent technologies for 3-dimensional image-guided radiation delivery," Semin. Radiat. Oncol. 15(3), 208-216 (2005).

Jia, X et al., "GPU-based fast cone beam CT reconstruction from undersampled and noisy projection data via total variation," Med. Phys. 37(4), 1757-1760 (2010).

Jia, X et al., "GPU-based fast low-dose cone beam CT reconstruction via total variation," J. X-Ray. Sci. Tech. (in press 2011).

Park, J. C. et al., "Four-dimensional cone-beam computed tomography and digitial tomosynthesis reconstructions using respiratory signals extracted from transcutaneously inserted metal markers for liver SBRT," Med. Phys. 38(2), 1028-1036 (2011).

Ritschl, L. et al., "Improved total variation-based CT image reconstruction applied to clinical data," Phys. Med. Biol. 56(6), 1545-1561 (2011).

Sidky, E. Y. et al., "Image reconstruction in circular cone-beam computed tomography by constrained, total-variation minimization," Phys. Med. Biol. 53(17), 4777-4807 (2008).

Song, W. Y. et al., "A dose comparison Songstudy between XVI and OBI CBCT systems," Med. Phys. 35(2), 480-486 (2008).

Song, W. Y. Song et al., "Image-guided adaptive radiation therapy (IGART): Radiological and dose escalation considerations for localized carcinoma of the prostate," Med. Phys. 32(7), 2193-2203 (2005).

Szczykutowicz, T. P. et al., "Dual energy CT using slow kVp switching acquisition and prior image constrained compressed sensing," Phys. Med. Biol. 55(21), 6411-6429 (2010).

Tang, J. et al., "Performance comparison between total variation (TV)-based compressed sensing and statistical iterative reconstruction algorithms," Phys. Med. Biol. 54(19), 5781-5804 (2009).

Wang, J. et al., "Iterative image reconstruction for CBCT using edge-preserving prior," Med. Phys. 36(1), 252-260 (2009).

Xu, F. et al., "Accelerating popular tomographic reconstruction algorithms on commodity PC graphics hardware," Trans. Nucl. Sci. 52(3), 654-663 (2005).

* cited by examiner

IMAGE RECONSTRUCTION USING GRADIENT PROJECTION FOR MEDICAL IMAGING APPLICATIONS

CROSS-REFERENCE TO RELATED PATENT APPLICATIONS

This patent document is a 35 USC §371 National Stage application of International Application No. PCT/US2012/029591, filed on Mar. 18, 2012, which claims the benefit of priority from U.S. Provisional Patent Application Ser. No. 61/454,387, entitled "FAST, ITERATIVE, IMAGE RECONSTRUCTION USING GRADIENT PROJECTION FOR MEDICAL IMAGING APPLICATION," filed on Mar. 18, 2011, the entire contents of which are incorporated by reference in the present patent application.

BACKGROUND

This application relates to devices and techniques that use medical imaging technologies.

Cone-beam computed tomography (CBCT) can be used in radiation therapy to provide precise on-line positioning (and on-line/off-line re-planning) of patients. This is possible due to the wealth of information contained in the three-dimensional (3D)-CBCT images including 1) anatomic information, 2) geometric information, and 3) CT numbers for possible dose calculations for treatment verifications and plan re-optimizations. Therefore, the more the scans are taken, generally the better quality treatments that can be administered.

However, more scans typically expose an underlying subject to more radiation.

Better CBCT image reconstruction methods are desired.

SUMMARY

Techniques and systems and apparatus are disclosed for implementing medical imaging technology.

The subject matter described in this specification potentially can provide one or more of the following advantages. For example, the described algorithm can converge faster than any iterative algorithms to date, at the same time, to potentially achieve reduction in input signal data necessary for reconstruction. Fast reconstruction time can make this method readily applicable/practical to routine clinical use in Medicine, Dentistry, Radiology, and Radiation Oncology. Also, the described techniques can potentially reduce the radiation exposure for the patients while achieving equivalent image quality compared with conventional techniques.

In one exemplary aspect, a disclosed method for estimating an unknown image from a plurality of cone-beam computed tomography (CBCT) image projections includes estimating the unknown image by solving for a minima of a function comprising a fidelity term that is based on the plurality of image projections and a regularization term that is responsive to a sparsity of the CBCT image projections. The step of solving comprises iteratively estimating the minima of the function by calculating a projected image gradient of the function, determining a step size based on a Barzilai-Borwein (BB) formulation and adjusting the minima estimate using the gradient and a step size.

In another exemplary aspect, a disclosed apparatus for estimating an unknown image from a plurality of cone-beam computed tomography (CBCT) image projections includes an imager that obtains the plurality of CBCT image projections and a processors that estimates the unknown image by solving for a minima of a function comprising a fidelity term that is a function of the plurality of image projections and a regularization term that is responsive to a sparsity of the CBCT image projections. The step of solving comprises iteratively estimating the minima of the function by: calculating a projected image gradient of the function, determining a step size based on a Barzilai-Borwein (BB) formulation; and adjusting the minima estimate using the gradient and a step size.

BRIEF DESCRIPTION OF THE DRAWINGS

Like reference symbols and designations in the various drawings indicate like elements.

DETAILED DESCRIPTION

Figure 1:
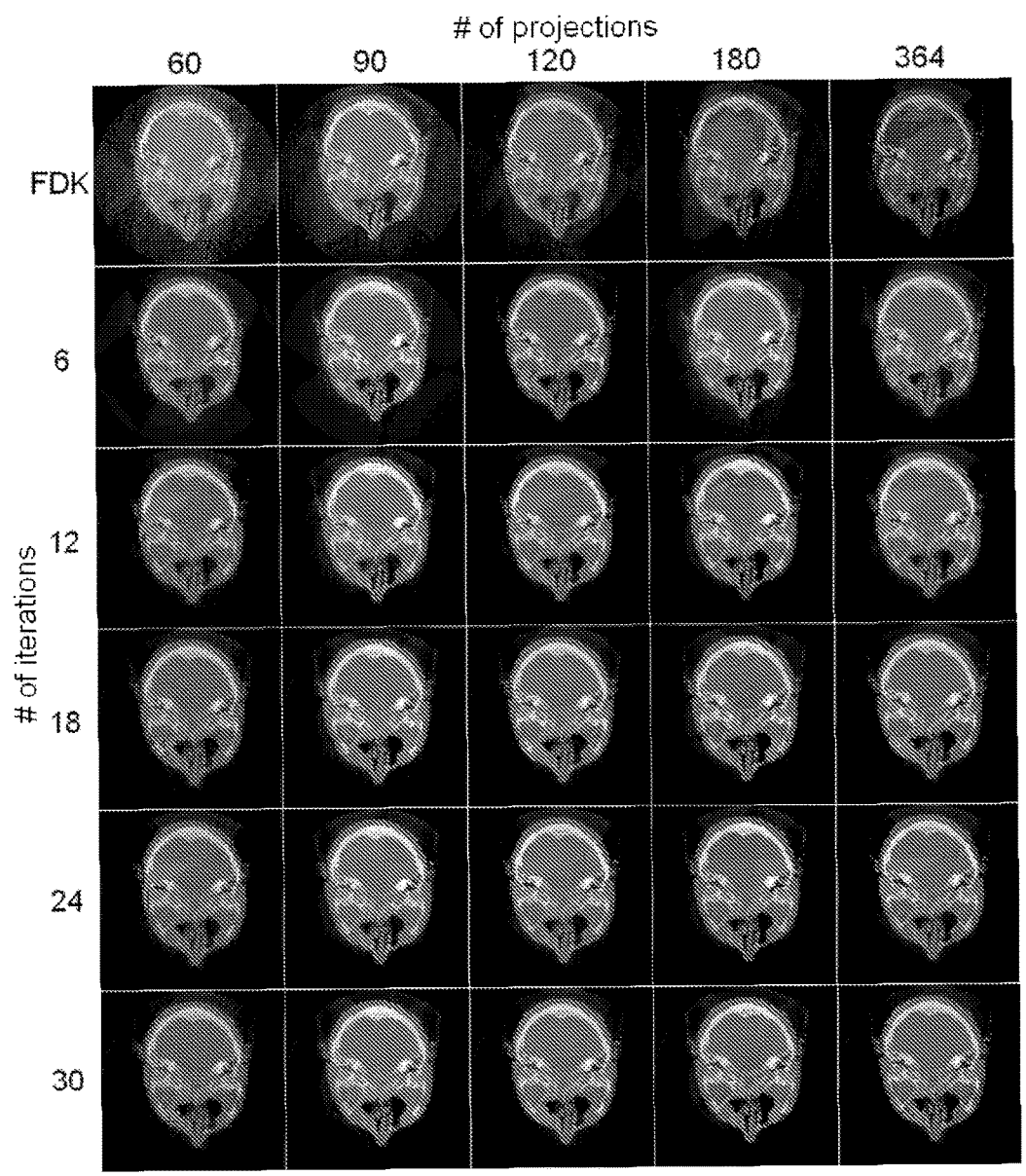
FIG. 1 shows reconstructed images as a function of number-of-projections and number-of-iterations. The window and level were kept the same for all images.

In recent years, the introduction of cone-beam computed tomography (CBCT) in radiation therapy has enabled precise on-line positioning (and on-line/off-line re-planning) of patients. This is possible due to the wealth of information contained in the three-dimensional (3D)-CBCT images including 1) anatomic information 2) geometric information and 3) CT numbers for possible dose calculations for treatment verifications and plan re-optimizations. Therefore, the more the scans are taken, generally the better quality treatments that can be administered.

Because CBCT uses ionizing X-rays to image, however, there is a legitimate concern of hazardous radiation exposure to patients. Due to this, the excessive use should be avoided and the benefits-to-harms ratio should be carefully weighed and debated for each treatment, especially for pediatric patients. This concern has now become an issue of central importance in North America, not only in radiation oncology, but in broader radiology community (e.g., Image Wisely™ and Image Gently™ campaigns).

The techniques, apparatus and systems described in this application can be used to implement CBCT reconstruction. In some implementations, the disclosed techniques advantageously allow rapid reconstruction of 3D images for diagnostic purpose, thereby reducing patient wait time. In some implementations, the disclosed techniques are useful in reducing the number of radiation scans to be taken of the subject, thereby reducing a patient's exposure to radiation.

Recently introduced compressed sensing theory has enabled accurate, low-dose cone-beam computed tomography (CBCT) reconstruction of anatomic information with fewer and noisier projections data. However, the reconstruction time remains a significant challenge for practical implementation in a busy clinic. The gradient projection algorithm disclosed in this patent document is based on Barzilai and Borwein formulation (GP-BB). In one aspect, the disclosed techniques handle the total variation (TV)-norm regularization-based least squares problem for CBCT reconstruction in an extremely efficient manner, with speed acceptable for use in on-line image-guided radiation therapy (IGRT).

In some implementations, CBCT is reconstructed by minimizing an energy function. In some implementations, the energy function includes a data fidelity term and TV-norm regularization term. In some implementations, both these terms are simultaneously minimized by calculating the gradient projection of the energy function. The step size at each iteration is determined using an approximate second-order Hessian calculation at each iteration, based on a Barzilai and Borwein formulation. To speed up the process, a multi-resolution optimization is used. In addition, the entire algorithm was designed to run with a single graphics processing unit (GPU) card (NVIDIA GTX 295, Santa Clara, Calif.).

To evaluate the performance, the CBCT projection data of a clinically-treated head-and-neck patient was acquired from the TrueBeam™ system (Varian Medical Systems, Palo Alto, Calif.). Evenly spaced angles were sub-sampled and used for varying the number of projections for image reconstruction.

The disclosed GP-BB algorithm was shown to be extremely efficient that a clinically reasonable patient image, using 120 CBCT projections, was reconstructed in ≤12 iterations for a total time of <34 seconds. The image quality was visually equivalent to the conventional Feldkamp-Davis-Kress (FDK) algorithm using 364 CBCT projections. This represents dose reduction of one-third (=120/364) all at while maintaining the speed needed for clinical use. By contrast, conventional solutions such as GE software (VEO) take about ~20 min to 2 hrs to find a solution.

In one aspect, the execution time of <34 seconds, with a single GPU card, makes the disclosed techniques entirely practical for daily clinical use.

There are rather straightforward ways to reduce imaging dose for CBCT, that is, either 1) minimize number of X-ray projections, 2) reduce the current setting in the X-ray tube (mA), and/or 3) reduce the total exposure time (ms). With the currently-standard Feldkamp-Davis-Kress (FDK) reconstruction algorithm, however, reducing the projections would cause aliasing artifact.

FIG. 1 depicts results obtained using the FDK reconstruction algorithm. The aliasing artifacts are visible, the severity of which depends inversely on the number of projections, and if mA and/or ms is reduced, noise in the image would increase. Both of these properties of FDK are extremely undesirable, especially if the images are used for guiding precise radiation therapy for cancer eradication.

In recent years, exciting advances in compressed sensing theory has shown that sparse signals (at least in some known transform domain) can be reconstructed from much smaller number of samples than Nyquist frequency would mandate. In other words, this means that (nearly) ideal images can be reconstructed from well-under-sampled projections, which in turn, means that the imaging dose can be safely reduced without compromising image quality. Past work has shown that, for CT-type reconstructions (both fan- and cone-beam), the total variation (TV) formulation's been particularly useful in exploiting the prior knowledge of minimal variation in X-ray attenuation characteristics across human body. To implement this method practically, however, has remained to be a challenge until now.

The main problem is the iterative nature of solving the TV-based compressed sensing formulation, which generally requires multiple iterations of forward and backward projections of large datasets in clinically feasible time frame (e.g., <1 min). Solving this rather cumbersome problem would require multiple innovations encompassing 1) computationally efficient parallel-programming with proper hardware to 2) mathematically formulating an efficient search algorithm for fast-solution-convergence. The former issue has been resolved successfully with the use of graphics processing units (GPU). This approach reduced the computational time from several hours to few minutes. The techniques disclosed in this document, in some implementations, provide a solution to the latter issue, such that, in combination with GPU programming, a realistic CBCT image quality is provided within a clinically acceptable reconstruction times for on-line IGRT.

Methods and Materials

The image reconstruction problem can be formulated as a problem to solve a constrained convex optimization problem of the form:

$$\min_x f(x) = \|Ax - b\|_2^2 + \lambda R(x) \text{ while enforcing } x \geq 0 \quad (1a)$$

where R(x) is R(x) is a regularization term serving as a sparsity promoting prior. For example, a common choice for R(x) is a total variation L1-norm. In one example implementation, the term R(x) can be selected to be:

$$\min f(x) = \|Ax - b\|_2^2 + \lambda \|TV(x)\|_1^1 \text{ while enforcing } x \geq 0 \quad (1b)$$

where x=unknown CBCT volume image, A=Radon transform operator, b=measured projections data, λ=regularization constant, and TV=Total Variation regularization term on j, and k axis defined by:

$$TV(x) = \sum_{i,j,k} \sqrt{[x(i+1, j, k) - x(i, j, k)]^2 + [x(i, j+1, k) - x(i, j, k)]^2 + [x(i, j, k+1) - x(i, j, k)]^2} \quad (2)$$

In its form, the first term (fidelity term) enforces fidelity of x to the measured projections data and the second term (regularization term) promotes sparsity inherent in the X-ray attenuation characteristics of human body (i.e., CBCT volume image).

A gradient projection algorithm that iteratively seeks a solution to Equation 1 in the direction of the projected gradient all at while enforcing non-negativity of the found solution can be solved as follows. That is, Equation 1 can be solved iteratively using:

$$x_{k+1} = [x_k - \alpha_k p_k]^+ \text{ where } [*]^+ = \max[*, 0] \quad (3)$$

and $$p_k = g_k \text{ if } g_k \leq 0 \text{ or } x_k \geq 0$$

$$p = 0 \text{ otherwise} \quad (4)$$

where $\alpha_k$=step size at iteration k, and $p_k$=projected gradient of function $f(x_k)$. Here, $g_k$ is the gradient of $f(x_k)$ defined as:

$$g_k = A^T(Ax_k - b) + \lambda \nabla_k(TV(x_k)) \quad (5)$$

where $A^T$ is the transpose operator of Radon transform matrix A, which is physically interpreted as a back-projection operation on x.

In iteratively solving Equation 3, the speed of convergence is dependent on choosing a proper "step-size"$\alpha_k$ at each iteration. It will be appreciated that the less the number of iterations used to find the optimal solution x*, the less the number of times one needs to calculate A and $A^T$, which are computationally very expensive. There are few approaches in choosing an appropriate $\alpha_k$ including 1) a fixed $\alpha_k$ throughout, and 2) a backtracking line-search method that satisfies the Armijo condition. The first method is not trivial in finding an optimal value as convergence speed and image quality is inversely proportional. The second method is popular and guarantees a monotonic convergence but incurs relatively high computational burden as the backtracking line-search to satisfy Armijo condition is an iterative process in itself (i.e., iteration within iteration).

In some implementations, an approximate second-order solver, where the objective function may not be monotonically decreasing as in backtracking line-search, but much faster convergence is achieved, is used. A similar approach was proposed by Barzilai and Borwein (BB) in areas unrelated to medical imaging. In one aspect, the disclosed technique calculates each step with the formula (compare to Equation 3):

$$x_{k+1} = [x_k - H_k^{-1} p_k]^+ \quad (6)$$

where $H_k$ is an approximation to the true Hessian of f(x) at $x_k$ (i.e., approximate second-order solver). To calculate $H_{k-1}$, the BB method makes a simple approximation to the Hessian by setting $H_k = \eta(k)I$, where I denotes an identity matrix and $\eta(k)$ is chosen to approximate the true Hessian over the most recent two iteration steps as:

$$p_k - p_{k-1} \approx \eta^{(k)}[x_k - x_{k-1}] \quad (7)$$

where $\eta^{(k)}$ is calculated at each iteration that satisfies Equation 7. In practical implementation, the optimal $\eta^{(k)}$ is solved in least squares sense by:

$$\eta^{(k)} = \frac{[x_k - x_{k-1}]^T[p_k - p_{k-1}]}{\|x_k - x_{k-1}\|_2^2} \quad (8)$$

Then, once $\eta^{(k)}$ is calculated, the Equation 6 is updated by:

$$x_{k+1} = [x_k - (\eta^{(k)})^{-1} p_k]^+ \quad (9)$$

The advantage of this technique is that, first, at each iteration, only $x_{k-1}$ and $p_{k-1}$ can be carried over to calculate $\eta^{(k)}$, which must be calculated in the previous step anyway. Thus, there are no "extra" calculations that need to be performed, which affects the speed of the optimization much favorably. Second, as found in original BB publication, the convergence of Equation 6 should be faster than the standard first-order methods such as the backtracking line-search discussed above. And, finally, since the entire $f(x)$ is minimized simultaneously in Equation 1 (and not alternatively as in conventional algorithms), the overall complexity of implementation is simplified while still guaranteeing optimal solution.

In some implementation, the above-described Gradient-Projection-Barzilai-Borwein (GP-BB) method, can be further sped up by adopting the following:

A. For k=0, initialize $x_{k=0}$=FDK. This results in faster convergence compared with setting $x_{k=0}$=0.

B. For k=0, initialize $(\eta^{(k=0)})^{-1}$ as:

$$(\eta^{(0)})^{-1} = \frac{p_k^T g_k}{\|A p_k\|_2^2} \quad (10)$$

since $x_{k-1}$ and $p_{k-1}$ in Equation 8 doesn't exist. Note that Equation 10 is the close form solution for the optimal step size for minimizing the first term of Equation 1.

Based on the discussion above, in some implementations, the following gradient descent method can be used.

Step 1: (Initialization) given $x_0$ and set k=0
Step 2: Calculate $g_k$ and project the gradient to acquire $p_k$
Step 3: if k=0 initialize $\eta^{(0)}$ else calculate $\eta(k)$
Step 4: update $x_{k+1}$,
Step 5: let $x_{k+1}$=0 if $x_{k+1}$<0, k=k+1 and return to step 2

Here the $\eta(0)$ magnitude has to be initialized at the first iteration step since the value of $x_{k-1}$ and $p_{k-1}$ is unknown to calculate $\eta(0)$. This can be initialized by the closed form solution for the optimal step size of the gradient descent in the quadratic cost function which is given by $$(\eta^{(0)})^{-1} = \frac{\|g^{(k)}\|_2^2}{\|A(g^{(k)})\|_2^2}$$

Based on the discussion above, in some implementations, the following gradient projection method can be used.

Step 1: (Initialization) given $x_0$ and set k=0
Step 2: Calculate $g_k$ and project the gradient to acquire $p_k$
Step 3: if k=0 initialize $\eta^{(0)}$ else calculate $\eta(k)$
Step 4: update $x_{k+1}$,
Step 5: let $x_{k+1}$=0 if $x_{k+1}$<0, k=k+1 and return to step 2

Here the $\eta^{(0)}$ magnitude has to be initialized at the first iteration step since the value of $x_{k-1}$ and $p_{k-1}$ is unknown to calculate $\eta(0)$. This can be initialized by the closed form solution for the optimal step size of the gradient descent in the quadratic cost function which is given by the equation above.

The above iterations are performed until a termination criterion is met (e.g., no further improvement in the estimate of x— or improvement falls below a threshold, expiration of a time, a number of iterations, etc.).

In some implementations, a two-resolution-level optimization is utilized. For example, in some implementations x is first set to a lower resolution (e.g., 256×256×70) volume, and optimized. Next, the result is resampled to a higher resolution (e.g., 512×512×70) volume for a second-level optimization. The resolution at level one and two are 0.97× 0.97×2.0-mm and 0.49×0.49×2.0-mm, respectively.

In some implementations, the entire code can be structured and implemented in C with CUDA programming environment (NVIDIA, Santa Clara, Calif.) to utilize the massive parallel computational capability of GPU hardware. In one example, a single GTX 295 card that consists of 480 processing cores with 1.24 GHz clock speed and 1,792 MB memory is used. In terms of CPU, an Intel Core™ i7 with 2.68 GHz clock speed, 12.0 GB DDR3 RAM, on a 64-bit Window 7 OS is usable. In short, the most time consuming operations $[Ax_k]$ and $[A^T(Ax_k-b)]$ are parallelized by assigning each detector pixel values and image voxel values as threads in GPU.

To evaluate the performance of the disclosed algorithm, the CBCT projection data of a clinically-treated head-and-neck patient was acquired from the TrueBeam™ system (Varian Medical Systems, Palo Alto, Calif.). In total, 364 projections were acquired in a 200-degree rotation. The imager has 1024×768 pixels with 0.388×0.388-mm resolution. This was down-sampled to 512×384 pixels with 0.776× 0.776-mm for reconstruction. Evenly spaced angles were sub-sampled and used for varying the number of projections for image reconstruction.

Results and Discussion

The application of the BB method to solve the compressed sensing-type algorithms was based on inventors' non-obvious intuition. That is, conventional iterative algorithms for minimizing f(x), fail to exploit the inventors' observation that the Hessian of f(x) is well approximated by a scaled identity matrix ($\eta I$). The Hessian of the first term in f(x) is given by $A^T A$. The inventors realized that, in Computer Tomography applications, CBCT, DTS, PET, and SPECT, the columns of matrix A contain only few non-zero elements and, in most cases, the positions of the non-zero elements are different for each column. This implies that columns of matrix A are almost orthogonal. This suggests that the Hessian is close to a diagonal matrix and can be approximated by a scaled identity matrix. In case of Magnetic Resonance Imaging (MRI), the columns of matrix A are columns of an FFT matrix which is also (almost) orthogonal. Regarding the regularization term, the inventors made the observation that the Hessian of the regularization term is well approximated by a scaled identity matrix. Based on these observations, inventors have determined that the adoption of BB step size calculation would be effective in solving the compressed sensing-type image reconstruction algorithms since BB method works particularly effectively when Hessian can be well approximated by a scaled identity matrix.

Note that the use of BB method in some implementations makes gradient projection algorithm much more efficient. This is because determining a step size using the BB rule does not require iterative function evaluations of f(x) which is computationally expensive yet necessary for commonly used backtracking line-search based step size determination rules. Thus, the computational complexity at each iteration in GP-BB is much less than that of the gradient-projection method with backtracking line-search.

Furthermore, given that the first term in f(x) (least squares term) is quadratic, the optimal step size determination rule for a quadratic function given by Equation (2) above to determine the step size at the first iteration where BB rule is not applicable. This turns out to be very effective in accelerating initial convergence.

Finally, it will be appreciated that the step sizes are computed in a very GPU-friendly manner whether it is based on BB or otherwise. Multiplications and summations are separable and, therefore, great speed accelerations are possible when GPU computing power is available.

FIG. 1 shows in one-shot view of the various image qualities achieved as a function of number-of-projections and number-of-iterations used. The window and level were kept the same for all images. The first row shows the image qualities achieved with the FDK algorithm. As can be seen, and true for both FDK and GP-BB algorithms, as the number-of-projections increases, the image quality increases. And, as expected, as the number-of-iterations increases, the image quality increases as well for GP-BB algorithm. This also means that FDK-initialized GP-BB algorithm always does better than just the FDK alone, for any number-of-iterations.

Table 1 lists the reconstruction times recorded for each image volume shown in FIG. 1.

| Time [sec] | # of projections (views) used | | | | |
|---|---|---|---|---|---|
| # of iterations | 60 | 90 | 120 | 180 | 364 |
| FDK | 0.27 | 0.34 | 0.5 | 0.75 | 1.45 |
| 6 | 9.891 | 14.48 | 19.25 | 28.35 | 58.11 |
| 12 | 17.58 | 25.57 | 33.77 | 49.94 | 101.83 |
| 18 | 24.88 | 36.55 | 48.21 | 71.92 | 146.51 |
| 24 | 32.92 | 47.62 | 62.86 | 92.86 | 188.37 |
| 30 | 39.91 | 58.87 | 77.99 | 116.55 | 234.51 |

Assuming a clinically feasible time frame to ≤1 min (60 seconds), then up to about 120 projections with 18 iterations would be possible. Now, knowing this and looking back in FIG. 1 to search for a reasonable compromise between image quality and reconstruction time, the image with 120 projections, 12 iterations, and 33.77 seconds seems to fit the best.

Figure 2:
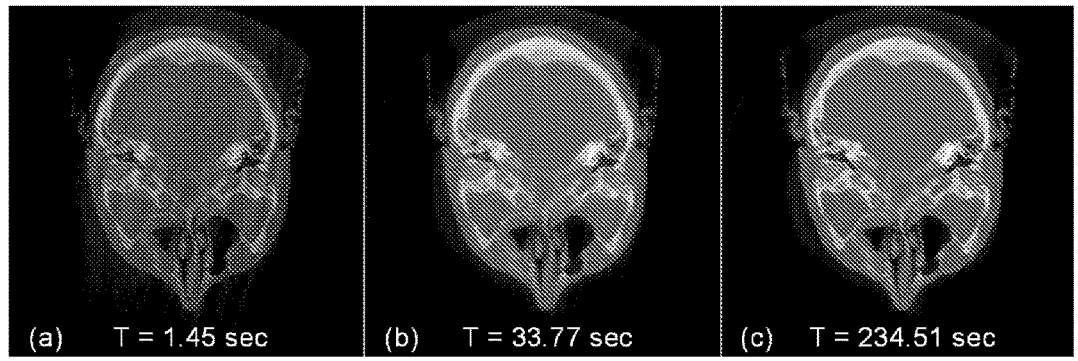
FIG. 2 shows selected images from FIG. 1; (a) FDK with 364 projections, (b) GP-BB with 12 iterations and 120 projections, and (c) GP-BB with 30 iterations and 364 projections. Reconstruction times are displayed on the images themselves.

FIG. 2 shows, in side by side, the clinical FDK image (364 projections), the best-fit GP-BB image (120 projections & 12 iterations), and the best GP-BB image (364 projections, 30 iterations) in FIG. 1. First of all, the best GP-BB image has visually better image quality than the FDK image, which reinforces the fact that GP-BB always enhances image quality. In another aspect, the image quality of the best-fit GP-BB image is visually comparable to the FDK image, and, with a reasonable reconstruction speed (i.e., 12 iterations in <34 seconds). Therefore, if the best-fit GP-BB image were to be used clinically, the dose would be cut by one-third (=120/364 projections), and one would still be able to use this in a clinically viable time frame of <34 seconds. To the best of our knowledge, this convergence speed achieved with our proposed GP-BB algorithm is the fastest compressed sensing-based algorithms that have been proposed for CBCT reconstruction to date.

The above-disclosed techniques can be applied to reconstruct images for computed tomography (CT), cone beam (CBCT), digital tomosynthesis (DTS), positron emission tomography (PET), single photon emission computed tomography (SPECT), and Magnetic resonance imaging (MRI) for diagnosis, prognosis, radiation treatment planning, and monitoring. Basically, any medical images with sparse sampling of data and use of iterative image reconstruction (including use of sparsity promoting prior) can benefit from using our method to fast reconstruct an optimal image.

Figure 3:
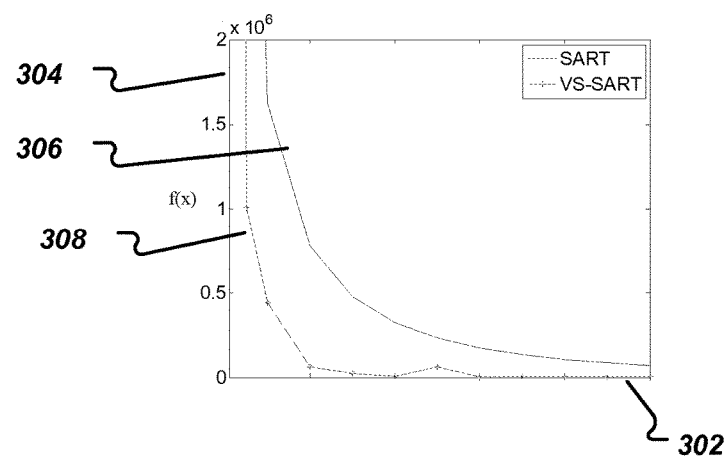
FIG. 3 is a graph depicting the effects of the use of variable step size on convergence of the iterative image restoration algorithm.

FIG. 3 compares the effects of the above-discussed calculation of variable step size in each iteration (VS-SART) compared to the use of constant step size (SART) in each iteration. The horizontal axis 302 representations number of iterations and the vertical axis 304 represents the minima at a given iteration of the function f(x) for curve 306 corresponding to SART and curve 308 corresponding to VS-SART. As shown in FIG. 3, as the iterations progress, f(x) is asymptotically minimized for both algorithms but VS-SART is found to converge much faster.

Figure 4:
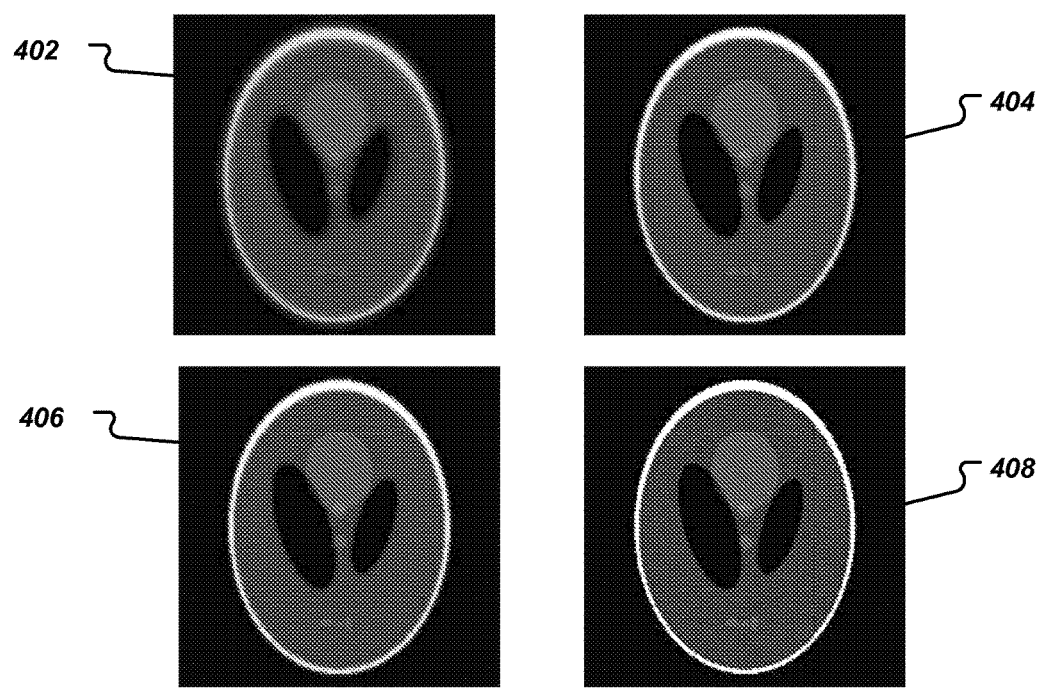
FIG. 4 shows image reconstruction results after 20 and 60 iterations.

FIG. 4 shows the resulting image quality after 20 and 60 iterations. It is evident that VS-SART commands superior image quality for a given iterations. . Shepp-Logan numerical phantom reduction images with 180 parallel-beam projections—(402) SART, 20 iterations, (404) VS-SART, 20 iterations, (406) SART, 60 iterations, (408) VS-SART, 60 iterations.

Figure 5:
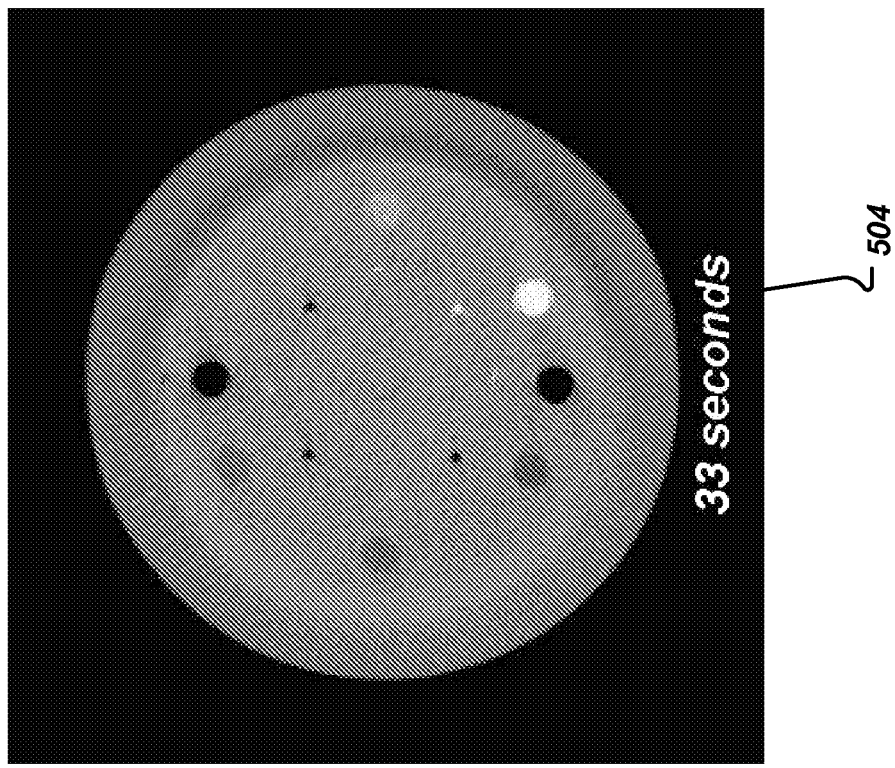
FIG. 5 shows the estimated image results for one implementation of an image restoration algorithm.
Figure 5:
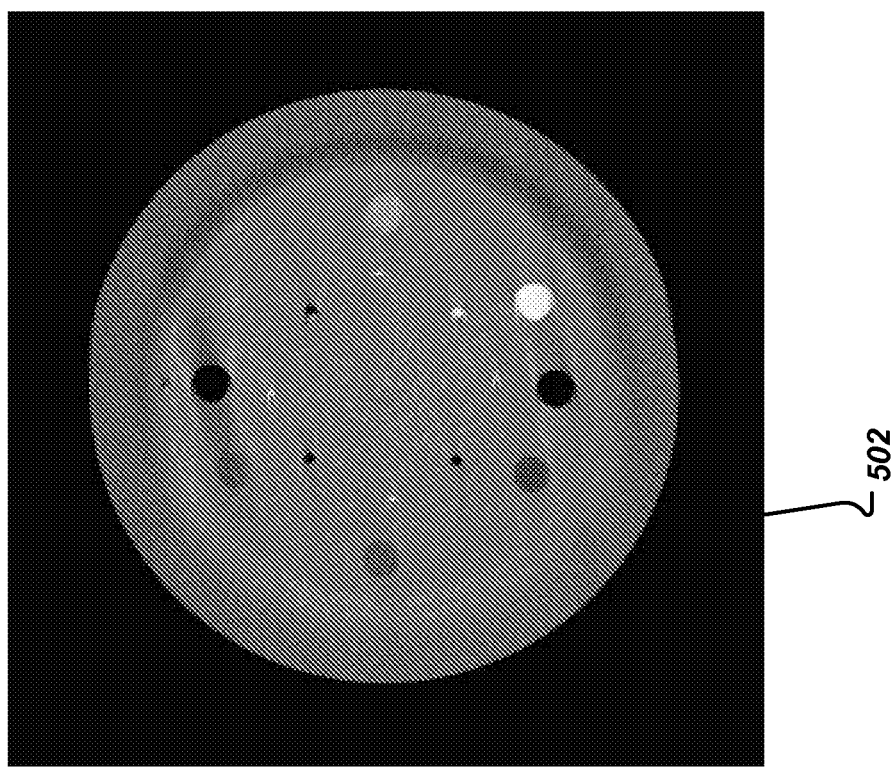

FIG. 5 shows the results for the physical CatPhan phantom. Compared with the commercial FDK algorithm with 364 projections, our VS-SART algorithm produces visibly equivalent quality CBCT image with only 120 projections, in 12 iterations completed in 33 seconds. This is a factor of three dose reduction while maintaining the reconstruction time acceptable. (502) FDK with 364 projections, (504) VS-SART with 120 projections (12 iterations).

Figures 6, 7:
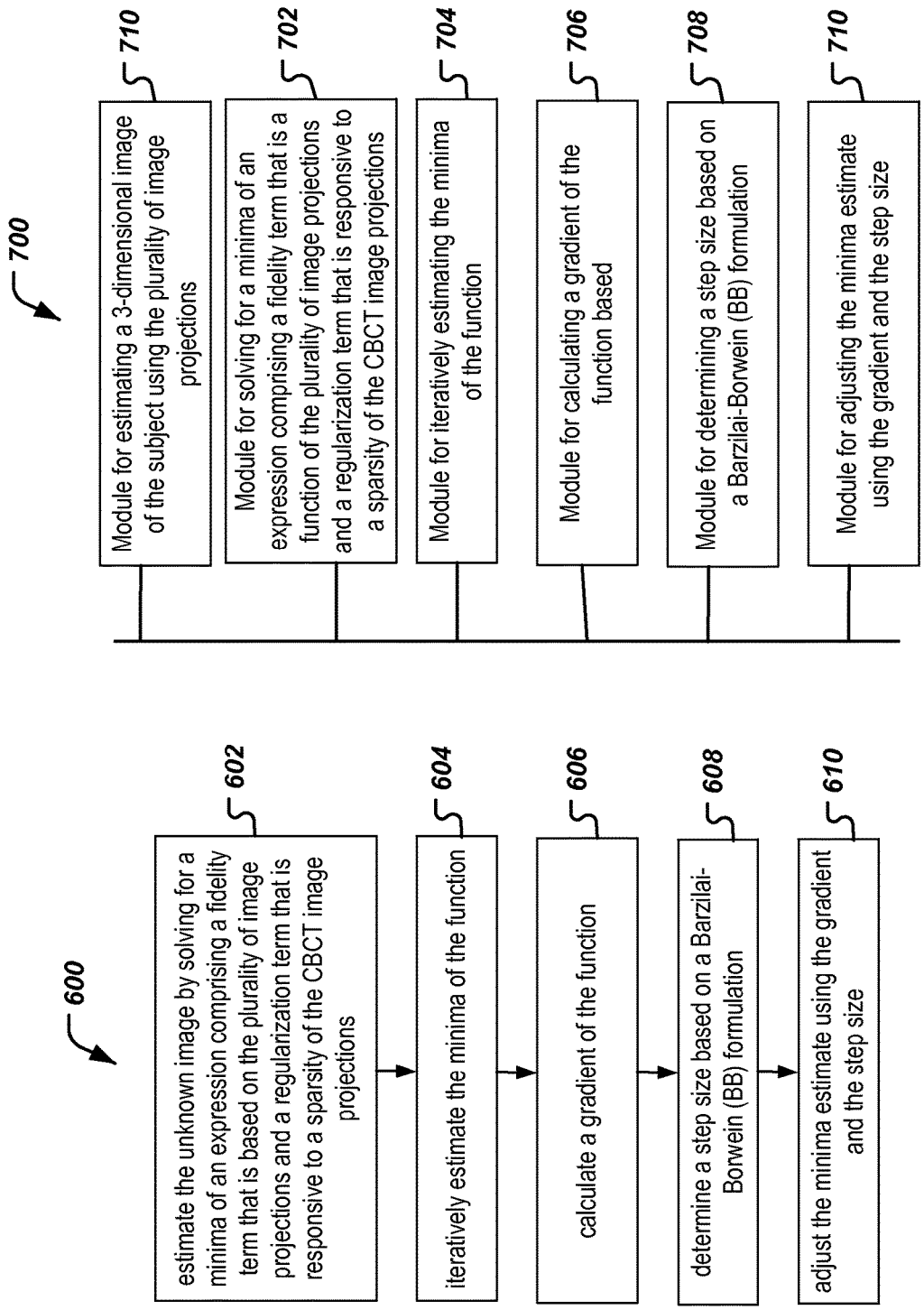
FIG. 6 is a flow chart representation of a process of estimating an unknown image from a plurality of cone-beam computed tomography (CBCT) image projections.
FIG. 7 is a block diagram representation of an apparatus that estimates an unknown image from a plurality of cone-beam computed tomography (CBCT) image projections.

FIG. 6 is a flow chart representation of a method of estimating an unknown image from a plurality of cone-beam computed tomography (CBCT) image projections. At 602, the unknown image is estimated by solving for a minima of an expression comprising a fidelity term that is based on the plurality of image projections and a regularization term that is responsive to a sparsity of the CBCT image projections. The solving for the minima is performed as follows: At 604, the minima of the function is iteratively estimated by repeating 606, 608 and 610, until a termination criterion is met. At 606, a gradient of the function is calculated. At 608, a step size is determined based on a Barzilai-Borwein (BB) formulation. At 610, the minima estimate is adjusted using the gradient and a step size. In some implementations, the gradient is a projected gradient of the function.

FIG. 7 is a block diagram representation of an apparatus 700 for estimating an unknown image from a plurality of cone-beam computed tomography (CBCT) image projections. The module 710 is for estimating a 3-dimensional image of the subject using the plurality of image projections. The module 702 is for solving for a minima of an expression comprising a fidelity term that is a function of the plurality of image projections and a regularization term that is responsive to a sparsity of the CBCT image projections. The module 704 is for iteratively estimating the minima of the function. The module 706 is for calculating a gradient of the function. The module 708 is for determining a step size based on a Barzilai-Borwein (BB) formulation. The module 710 is for adjusting the minima estimate using the gradient and the step size.

In one aspect, the fast reconstruction time makes the disclosed techniques readily applicable/practical to routine clinical use in Medicine, Dentistry, Radiology, and Radiation Oncology. In another aspect, a reduction in the radiation exposure for the patients while achieving equivalent image quality compared with conventional techniques.

It will be appreciated that, a low-dose CBCT reconstruction algorithm is disclosed. The major finding was that a clinically viable image can be obtained within 12 iterations and 34 seconds, and simultaneously cutting the dose by one-third. This makes our GP-BB algorithm entirely practical for daily clinical use.

It will further be appreciated that the disclosed compressed sensing-based algorithms enable, in one aspect, an accurate restoration of anatomic information with sparse and noisy sampled data. The Simultaneous Algebraic Reconstruction Technique (SART), i.e., simultaneously optimizing the two terms of energy function in expression in equation (1) above, reconstructs a volumetric image by iteratively conducting volume projection and correction back projection. SART-type algorithm is a special case of compressed sensing-type algorithms where the regularization term is absent.

The disclosed and other embodiments and the functional operations described in this document can be implemented in digital electronic circuitry, or in computer software, firmware, or hardware, including the structures disclosed in this document and their structural equivalents, or in combinations of one or more of them. The disclosed and other embodiments can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A method of estimating an unknown image from a plurality of cone-beam computed tomography (CBCT) image projections, the method comprising:
   estimating the unknown image in a lower resolution having a plurality of image voxels by solving for a minima of a function comprising a fidelity term that is based on the plurality of image projections and a regularization term that is responsive to a sparsity of the CBCT image projections; and
   resampling the lower resolution estimation to a higher resolution for a second-level estimation of the unknown image;
   wherein the step of solving comprises:
   iteratively estimating the minima of the function by:
   calculating a gradient of the function for each image voxel of the plurality of image voxels in parallel;
   determining a first step size based on a Radon transform operator, a projected gradient of the fidelity term, and a gradient of the fidelity term at a first iteration;
   determining a second step size based on a Barzilai-Borwein (BB) formulation including approximating a second-order Hessian of the function by a scaled identity matrix at each iteration after the first iteration, wherein the determining is performed without using an iterative search; and
   adjusting the minima estimate using the fidelity term and the first step size for the first iteration and using the gradient and the second step size after the first iteration.

2. The method of claim 1, wherein the gradient is a projected gradient of the function.

3. The method of claim 1, further comprising:
   initializing, for the first iteration, the minima estimate based on an optimization algorithm.

4. The method of claim 3, wherein the optimization algorithm comprises a Feldkamp-Davis-Kress (FDK) algorithm.

5. The method of claim 1, wherein the step of calculating the gradient includes:
   determining the gradient as a difference between a minima estimate in a current iteration and a minima estimate in a previous iteration, scaled by a scale factor.

6. The method of claim 1, wherein the determining the step size comprises:
   choosing the step size to be between a minimum value and a maximum value.

7. The method of claim 1, wherein the determining the step size comprises:
   choosing the step size based on a minima estimate in a previous iteration and a gradient in the previous iteration.

8. The method of claim 1, wherein the gradient is calculated without performing a matrix factorization.

9. The method of claim 1, wherein the unknown image comprises three dimensional (3D) anatomic information.

10. The method of claim 1, wherein the calculating a gradient of the function includes calculating a projected gradient of the function in the direction of the projected gradient while enforcing non-negativity of a solution.

11. The method of claim 1, wherein the estimating the unknown image by solving for the minima of the function includes optimizing the function for at least two resolution levels including a lower resolution volume of the image and a higher resolution volume of the image.

12. An apparatus for estimating an unknown image from a plurality of cone-beam computed tomography (CBCT) image projections, the apparatus comprising:
    an imager that obtains the plurality of CBCT image projections; and
    a processor that:
    estimates the unknown image in lower resolution having a plurality of image voxels by solving for a minima of a function comprising a fidelity term that is a function of the plurality of image projections and a regularization term that is responsive to a sparsity of the CBCT image projections; and
    resamples the lower resolution estimation to a higher resolution for a second-level estimation of the unknown image;
    wherein the step of solving comprises:
    iteratively estimating the minima of the function by:
    calculating a gradient of the function for each image voxel of the plurality of image voxels in parallel;
    determining a first step size based on a Radon transform operator, a projected gradient of the fidelity term, and a gradient of the fidelity term at a first iteration;
    determining a second step size based on a Barzilai-Borwein (BB) formulation including approximating a second-order Hessian of the function by a scaled identity matrix at each iteration after the first iteration without using an iterative search; and
    adjusting the minima estimate using the fidelity term and the first step size for the first iteration and using the gradient and the second step size after the first iteration.

13. The apparatus of claim 12, wherein the gradient is a projected gradient of the function.

14. The apparatus of claim 12, further comprising:
initializing, for the first iteration, the minima estimate based on an optimization algorithm.

15. The apparatus of claim 14, wherein the optimization algorithm comprises a Feldkamp-Davis-Kress (FDK) algorithm.

16. The apparatus of claim 12, wherein the step of calculating the gradient includes:
determining the gradient as a difference between a minima estimate in a current iteration and a minima estimate in a previous iteration, scaled by a scale factor.

17. The apparatus of claim 12, wherein the determining the step size comprises:
choosing the step size to be between a minimum value and a maximum value.

18. The apparatus of claim 12, wherein the determining the step size comprises:
choosing the step size based on a minima estimate in a previous iteration and a gradient in the previous iteration.

19. The apparatus of claim 12, wherein the gradient is calculated without performing a matrix factorization.

20. The apparatus of claim 12, wherein the unknown image comprises three dimensional (3D) anatomic information.

21. A computer program product comprising a non-transitory computer-readable medium having code stored thereon, the code, when executed by a computer, causing the computer to estimate an unknown image from a plurality of cone-beam computed tomography (CBCT) image projections, by:
estimating the unknown image in lower resolution having a plurality of image voxels by solving for a minima of an expression comprising a fidelity term that is a function of the plurality of image projections and a regularization term that is responsive to a sparsity of the CBCT image projections; and
resampling the lower resolution estimation to a higher resolution for a second-level estimation of the unknown image;
wherein the step of solving comprises:
iteratively estimating the minima of the function by:
calculating a gradient of the function for each image voxel of the plurality of image voxels in parallel;
determining a first step size based on a Radon transform operator, a projected gradient of the fidelity term, and a gradient of the fidelity term at a first iteration;
determining a second step size based on a Barzilai-Borwein (BB) formulation including approximating a second-order Hessian of the function by a scaled identity matrix at each iteration after the first iteration without using an iterative search; and
adjusting the minima estimate using the fidelity term and the first step size for the first iteration and using the gradient of the function and the second step size after the first iteration.

22. An imaging apparatus for estimating an unknown image from a plurality of cone-beam computed tomography (CBCT) image projections, comprising:
means for estimating a three-dimensional image of the subject in lower resolution having a plurality of image voxels using the plurality of image projections and resampling the lower resolution estimation to a higher resolution for a second-level estimation of the three-dimensional image, comprising:
means for solving for a minima of an expression comprising a fidelity term that is a function of the plurality of image projections and a regularization term that is responsive to a sparsity of the CBCT image projections;
wherein the means for solving includes:
means for iteratively estimating the minima of the function;
means for calculating a gradient of the function for each image voxel of the plurality of image voxels in parallel;
means for determining a first step size based on a Radon transform operator, a projected gradient of the fidelity term, and a gradient of the fidelity term at a first iteration;
means for determining a second step size based on a Barzilai-Borwein (BB) formulation including approximating a second-order Hessian of the function by a scaled identity matrix at each iteration after the first iteration without using an iterative search; and
means for adjusting the minima estimate using the fidelity term and the first step size for the first iteration and using the gradient of the function and the second step size after the first iteration.

\* \* \* \* \*